United States Patent [19]

Rubino et al.

[11] Patent Number: 5,493,060
[45] Date of Patent: Feb. 20, 1996

[54] METHOD OF MAKING 1,1-BIS-(4-HYDROXYPHENYL)-3,3,5-TRIMETHYLCYCLOHEXANE

[75] Inventors: Mark R. Rubino, Monroeville; Jeffrey S. Salek, Oakdale Borough, both of Pa.

[73] Assignee: Aristech Chemical Corporation, Pittsburgh, Pa.

[21] Appl. No.: 307,127

[22] Filed: Sep. 16, 1994

[51] Int. Cl.$^6$ ............................ C07C 39/17; C07C 37/00
[52] U.S. Cl. ............................................ 568/721; 568/718
[58] Field of Search ...................................... 568/721, 718

[56] References Cited

U.S. PATENT DOCUMENTS

| | | | |
|---|---|---|---|
| 2,602,821 | 7/1952 | Luten, Jr. et al. | 260/619 |
| 3,437,637 | 4/1969 | Matzner | 568/721 |
| 3,919,330 | 11/1975 | Kwantes et al. | 260/619 R |
| 4,201,878 | 5/1980 | Mark et al. | 568/723 |
| 4,964,890 | 10/1990 | Reuter et al. | 55/158 |
| 4,982,014 | 1/1991 | Freitag et al. | 568/721 |

FOREIGN PATENT DOCUMENTS 4003437  8/1991  Germany.

Primary Examiner—Werren B. Lone
Attorney, Agent, or Firm—William L. Krayer

[57] ABSTRACT

This invention provides a unique method of producing 1,1-bis-(4-hydroxyphenyl)-3,3,5-trimethylcyclohexane ("BPTMC"). The disclosed method manufactures BPTMC from ketals and hemithioketals of 3,3,5-trimethylcyclohexanone ("TMC"). The reaction takes place in the presence of an acid catalyst, and optionally added co-catalysts. Additionally, applicants have disclosed a particularly useful method of manufacturing BPTMC from TMC and alcohol and/or thiol starting materials. These starting materials react to form the TMC ketal or thioketal materials. This method is particularly useful in that it allows recovery and recycling of the alcohol and/or thiol.

14 Claims, No Drawings

METHOD OF MAKING 1,1-BIS-(4-HYDROXYPHENYL)-3,3,5-TRIMETHYLCYCLOHEXANE

TECHNICAL FIELD

This invention relates to the manufacture of 1,1-bis-(4-hydroxyphenyl)- 3,3,5-trimethylcyclohexane (herein referred to as "Bisphenol TMC" or "BPTMC"). In particular, this invention relates to an improved method of manufacturing BPTMC by the use of ketals, vinylic ethers, and/or analogous materials where sulfur is substituted for one oxygen atom. These starting materials are derived from 3,3,5-trimethylcyclohexanone (herein "TMC"). The derivatives are reacted with phenol in the presence of an acid catalyst and an optionally added cocatalyst.

BACKGROUND OF THE INVENTION

U.S. Pat. Nos. 4,964,890, 4,982,014, and 5,210,328 disclose methods of making BPTMC by condensing phenol with TMC in the presence of an acid catalyst. An organosulfur cocatalyst may also be used. These disclosures use TMC and ether ketones. They do not use the starting materials of applicants' disclosure.

Ketones are not the only known starting materials for making bisphenols. U.S. Pat. No. 4,201,878 teaches a method using ketals and alkenyl ethers. However, the U.S. Pat. No. '878 disclosure only includes ketals of unbranched cyclic ketones. The rapid formation of BPTMC in the present invention is surprising, and it is not predictable from the disclosure of the U.S. Pat. No. '878.

The three methyl groups of TMC affect the properties of materials containing TMC in ways that are difficult to predict. For example, cyclohexanone and phenol form bisphenol Z much faster than TMC and phenol form BPTMC due to interference from the methyl groups on TMC [see Makromol. Chem., Rapid Commun., Vol. 12, pp. 95–99 (1991) and Angew. Chem. Int. Ed. Engl., Vol. 30, pp. 1598–1610 (1991)]. Similarly, the properties of bisphenol Z polycarbonate cannot be used to accurately predict the properties of BPTMC polycarbonate. U.S. Pat. No. 5,210,328 shows that TMC and 4-tert-butylcyclohexanone respond differently to water during condensation with phenol.

In U.S. Pat. No. 3,919,330 a reference is made to U.S. application Ser. No. 432,376 filed Jan. 10, 1974 in which bisphenol-A is reported to have been disclosed as made from the ketal of acetone and ethylene glycol. Again, the trimethyl structure of TMC creates unique physical and chemical properties. Formation of BPTMC is not predictable or obvious from the disclosure of bisphenol-A formation from ketal or vinyl ether starting materials. Additionally, applicants know of no precedent for the formation of BPTMC or any other bisphenol from hemithioketal starting materials.

SUMMARY OF THE INVENTION

We have invented a method of producing BPTMC from ketals, vinylic ethers, and thio-containing derivatives of TMC rather than TMC itself. The formula for BPTMC is shown below:

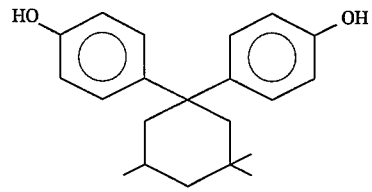

BPTMC forms faster from these starting materials than from the TMC, thus reducing or eliminating the need for organosulfur co-catalysts. Thus, the cost and difficulty of co-catalyst separation can be reduced or eliminated. Additionally, water is eliminated as a co-product. This results in enhanced changes such as reduced corrosiveness with an HCl catalyst.

The ketal, vinylic ether, or thio-containing starting material used will conform to the following formula:

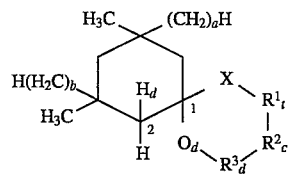

wherein,
X=oxygen or sulfur;
a=0,1; b=0,1; a+b=1;
c=0,1;
d=0,1; d≧c;
if d=0, there is a double bond between the number 1 and number 2 carbon of the ring;
t=0,1;
$R^1$, $R^2$, and $R^3$ are independent of one another and are each an alkyl, —OH substituted alkyl, or —SH substituted alkyl group; and
when c=0, $R^1$ and $R^3$ cannot be connected.

These starting materials are made by standard means known in the art. For example, TMC may be reacted with an alcohol or thiol to produce a desired starting material. Additional methods of ketal formation are well known in the art.

We have found that the use of thio-containing starting materials (known as hemithioketals and vinyl thioethers—VTE's—) for BPTMC formation combines two known effects of BPTMC formation in a novel way. The faster rate and higher selectivity known for both thiol co-catalysts and ketal-type starting materials are combined into one substance. The thiol containing group of the ketal-type material is released as the BPTMC formation proceeds, and it produces autocatalytic results.

In addition to the use of hemithioketals and VTE's as stoichiometric reagents for the formation of BPTMC, they may be added in co-catalytic amounts. The presence of the hemithioketal or VTE enhances formation of BPTMC from ketal, vinylic ether, or TMC starting material. This co-catalysis technique is unprecedented in the art.

DETAILED DESCRIPTION OF THE INVENTION

Our invention is thus a new method of manufacturing Bisphenol TMC. The method is accomplished as follows. The ketal, hemithioketal, vinylic ether, or VTE starting material is reacted with phenol. The reaction is conducted in the presence of an acid catalyst and optionally in the presence of a co-catalyst. The reaction produces BPTMC, and an organic alcohol is coproduced in place of water. This alcohol may be recycled, and used for starting material production.

We have found hydrochloric acid (HCl) to be an effective acid catalyst. Acid catalysis can be effectuated by the use of other acids well known in the art. For example, sulfuric acid, phosphoric acid, phosphorous pentoxide, hydrofluoric acid, hydrobromic acid, sulfonic acids, and strong cation exchange resins would all catalyze the reaction.

An unexpected finding in the course of experimentation is that organosulfur substances may be added to accelerate the reaction. However, as a matter of practice, organosulfur co-catalysts may not be desirable since sulfur contamination of the BPTMC can occur, and economic considerations make their use undesirable.

When a hemithioketal or VTE starting material is used unique results occur. The starting material reacts to produce an organosulfur co-catalyst. The reaction to BPTMC is thus enhanced by the presence of the co-catalyst. This autocatalytic-like process is completely novel and unobvious to the production of BPTMC.

Another unique process we have discovered is to use hemithioketals or VTE's in catalytic proportions to accelerate the reaction. Use of hemithioketal or VTE starting material as a co-catalyst is also new to BPTMC formation. The success encountered using hemithioketals and VTE's as autocatalysts and co-catalyst generators was completely unpredicted.

In applicants' invention, the starting material can be produced (among various methods known in the art) by reacting TMC with at least one alcohol or thiol. Applicants have found alcohols and thiols having the following formula to be effective:

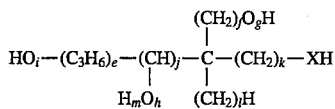

wherein:

e,g,h,j,k,l,m, and i=0,1 and are independent of one another except that: $h \leq j$;

when k+f=0, g=0;

when e=0, i+h<2; $m \geq h$; $m \leq j$;

f=0,1,2; and

X is oxygen or sulfur.

Specific examples of alcohols and thiols that may be used include, but are not limited to the following: ethylene glycol, propylene glycol, 1,3-propanediol, 2-methyl-1,3-propanediol, neopentyl glycol, 2,2,4-trimethyl-1,3-pentanediol, 2-ethyl-1,3-hexanediol, mercaptoethanol, 3-mercapto-1-propanol, 3-mercapto-1,2-propanediol, glycerol, and 2-ethylhexanol. In the preferred embodiment, the starting material is TMC ketal of ethylene glycol. The preferred acid catalyst is HCl, and is added in an amount of about 0.1 to 15 mol acid per mol starting material. The phenol to starting material ratio should be about 1:1 to 10:1. The original alcohol that is co-produced with BPTMC is recycled to a starting material production step.

The invention is illustrated but not limited by the following examples:

EXAMPLE 1

Two reactions were performed using TMC and TMC ketal of ethylene glycol (TMCEG)[1], respectively. The relative efficiency of BPTMC formation was studied.

Into a three-neck 500 ml round bottom flask equipped with an overhead stirrer, an HCl delivery tube, and an internal thermocouple, ketone/ketal (106.3 mmol) and molten phenol (45° C.; 637.6 mmol) were added with moderate stirring. HCl was bubbled directly into the reaction mixture at a rate of 0.9 mmol/min. The reaction temperature, initially about 40° C., was allowed to gradually cool to room temperature. The reactions were monitored as a function of time by gas chromatographic analyses. The results are displayed in Table I.

TABLE I

| Time, hr | Ratio[2] | |
| --- | --- | --- |
| | TMC | TMCEG |
| 1.0 |  | 63.05 |
| 2.0 | 174.5 | 17.60 |
| 3.0 |  | 7.08 |
| 4.0 | 61.19 | |
| 5.0 | | |
| 6.0 | 33.61 | |
| 22.0 | 8.12 | |

[1]TMC ketal of ethylene glycol:

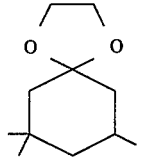

[2]Reaction aliquots were first silylated using N,O-bis(trimethylsilyl)acetamide in order to assay by gas chromatography. The "Ratio" heading represents the area % sum of starting materials (TMC/TMCEG and silylated phenol) divided by the area % of product (silylated BPTMC).

EXAMPLE 2

Two reactions were performed using TMCEG. The first reaction used 1-decanethiol as co-catalyst. The second reaction did not. The relative efficiency of BPTMC formation was examined.

Into a three-neck 500 ml round bottom flask equipped with an overhead stirrer, an HCl delivery tube, and an internal thermocouple, TMCEG (106.3 mmol), molten phenol (45° C.; 637.6 mmol), and 1-decanethiol (12.8 mmol) were added with moderate stirring. HCl was bubbled directly into the reaction mixture at a rate of 0.9 mmol/min. The reaction temperature, initially about 40° C., was allowed to gradually cool to room temperature. A second reaction was performed this way except no 1-decanethiol was added. The reactions were monitored as a function of time by gas chromatographic analyses. The results are displayed in Table II.

TABLE II

| Time, hr | Ratio* | |
| --- | --- | --- |
| | RSH added | no RSH added |
| 1.0 | 5.64 | 63.05 |
| 2.0 | 2.77 | 17.60 |
| 3.0 | 1.98 | 7.08 |

*Reaction aliquots were first silylated using N,O-bis(trimethylsilyl)acetamide in order to assay by gas chromatography. The "Ratio" heading represents the area % sum of starting materials (TMC/TMCEG and silylated phenol) divided by the area % of product (silylated BPTMC).

EXAMPLE 3

Two reactions were performed using TMC and TMCEG, respectively. 1-Decanethiol was added as a co-catalyst. The relative efficiency of BPTMC formation was determined.

Into a three-neck 500 ml round bottom flask equipped with an overhead stirrer, an HCl delivery tube, and an internal thermocouple, ketone/ketal (106.3 mmol), molten phenol (45° C.; 637.6 mmol), and 1-decanethiol (12.8 mmol) were added with moderate stirring. HCl was bubbled directly into the reaction mixture at a rate of 0.9 mmol/min. The reaction temperatures, initially about 40° C., were allowed to gradually cool to room temperature. The reactions were monitored as a function of time by gas chromatographic analyses. The results are displayed in Table III.

TABLE III

| Time, hr | Ratio* | |
|---|---|---|
| | TMC | TMCEG |
| 1.0 | | 5.64 |
| 2.0 | 3.05 | 2.77 |
| 3.0 | | 1.98 |
| 4.0 | 1.92 | |
| 6.0 | 1.75 | |

*Reaction aliquots were first silylated using N,O-bis(trimethylsilyl)acetamide in order to assay by gas chromatography. The "Ratio" heading represents the area % sum of starting materials (TMC/TMCEG and silylated phenol) divided by the area % of product (silylated BPTMC).

EXAMPLE 4

Two reactions were performed using TMC ketal of 2-ethyl-1-hexanol (TMCEH).[1] The first reaction used 1-octanethiol as a co-catalyst. The second reaction did not. The reactions were examined in terms of reaction efficiency and yield.

Into a three-neck 500 ml round bottom flask equipped with an overhead stirrer, an HCl delivery tube, and an internal thermocouple, TMCEH (106.3 mmol), molten phenol (45° C.; 637.6 mmol), and 1-decanethiol (10.6 mmol) were added with moderate stirring. HCl was bubbled directly into the reaction mixture at a rate of 0.6 mmol/min. The reaction temperature, initially about 40° C., was allowed to gradually cool to room temperature. The second reaction was peformed in the same manner except that 1-decanethiol was not added. Each reaction was monitored as a function of time by gas chromatographic analyses. After one day, the reaction mixtures were diluted with deionized water and suction filtered using a sintered glass Buchner funnel (4–5.5 μm pore diameter). The resulting filter cakes were triturated two times for one hour each using water at 80° C. The resulting products were dried for 16 hours in vacuo. The results are displayed in Table IV.

TABLE IV

| Run | Ratio[2] | | | | Yield |
|---|---|---|---|---|---|
| | 2 hr | 4 hr | 6 hr | 24 hr | |
| 1-octanethiol added | 7.12 | — | 5.38 | 3.39 | 74% |
| 1-octanethiol not added | 23.68 | 7.38 | 6.56 | 4.80 | 41% |

[1]TMC ketal of 2-ethyl-1-hexanol:

TABLE IV-continued

| Run | Ratio[2] | | | | Yield |
|---|---|---|---|---|---|
| | 2 hr | 4 hr | 6 hr | 24 hr | |

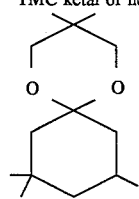

[2]Reaction aliquots were first silylated using N,O-bis(trimethylsilyl)acetamide in order to assay by gas chromatography. The "Ratio" heading represents the are % sum of starting materials (TMC/TMCEH and silylated phenol) divided by the area % of product (silylated BPTMC).

EXAMPLE 5

Three reactions were performed using TMCEG, TMC ketal of neopentyl glycol (TMCNPG),[1] and TMCEH, respectively. The reactions were examined in terms of reaction efficiency and yield.

Into a three-neck 500 ml round bottom flask equipped with an overhead stirrer, an HCl delivery tube, and an internal thermocouple, ketal (106.3 mmol) and molten phenol (45° C.; 637.6 mmol) were added with moderate stirring. HCl was bubbled directly into the reaction mixtures at a rate of 0.6 mmol/min. The reaction temperatures, initially about 40° C., were allowed to gradually cool to room temperature. The reactions were monitored as a function of time by gas chromatographic analyses. After one day, the reaction mixtures were diluted with deionized water and suction filtered using a sintered glass Buchner funnel (4–5.5 μm pore diameter). The resulting filter cakes were triturated two times for one hour each using water at 80° C. The resulting products were dried for 16 hours in vacuo. The results are displayed in Table V.

TABLE V

| Ketal | Ratio[2] | | | | Yield |
|---|---|---|---|---|---|
| | 2 hr | 4 hr | 6 hr | 24 hr | |
| TMCEG | 28.42 | 7.54 | 3.09 | 1.87 | 79% |
| TMCNGP | 46.78 | 11.87 | 8.76 | 4.26 | 36% |
| TMCEH | 23.68 | 7.38 | 6.56 | 4.80 | 41% |

[1]TMC ketal of neopentyl glycol:

[2]Reaction aliquots were first silylated using N,O-bis(trimethylsilyl)acetamide in order to assay by gas chromatography. The "Ratio" heading represents the area % sum of starting materials (TMC/ketal and silylated phenol) divided by the area % of product (silylated BPTMC).

EXAMPLE 6

Two reactions were performed using TMC. The first reaction used TMC hemithioketal of mercaptoethanol (TMCME)[1] as a co-catalyst. The second reaction did not.

The reactions were examined in terms of reaction efficiency and yield.

Into a three-neck 500 ml round bottom flask equipped with an overhead stirrer, an HCl delivery tube, and an internal thermocouple, TMC (106.3 mmol), molten phenol (45° C.; 637.6 mmol), and TMCME (10.6 mmol) were added with moderate stirring. HCl was bubbled directly into the reaction mixture at a rate of 0.6 mmol/min. The reaction temperature, initially about 40° C., was allowed to gradually cool to room temperature. The second reaction was performed in the same manner except that TMCME was not added. Each reaction was monitored as a function of time by gas chromatographic analyses. After one day, the reaction mixtures were diluted with deionized water and suction filtered using a sintered glass Buchner funnel (4–5.5 μm pore diameter). The resulting filter cakes were triturated two times for one hour each using water at 80° C. The resulting products were dried for 16 hours in vacuo. The results are displayed in Table VI.

TABLE VI

| Run | Ratio[2] | | | | Yield |
|---|---|---|---|---|---|
| | 2 hr | 4 hr | 6 hr | 24 hr | |
| TMCME added | 3.99 | 1.66 | 1.52 | 1.44 | 80% |
| TMCME not added | 28.42 | 7.45 | 3.09 | 1.87 | 79%[3] |

[1]TMC ketal of mercaptoethanol:

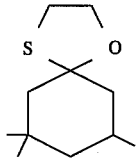

[2] Reaction aliquots were first silylated using N,O-bis(trimethylsilyl)acetamide in order to assay by gas chromatography. The "Ratio" heading represents the area % sum of starting materials (TMC and silylated phenol) divided by the area % of product (silylated BPTMC).
[3]A comparable yield was obtained in this case because the reaction was run for 24 hours. Ratio data confirm that the reaction rate was slower without TMCME added. If the reactions were worked up after 6 hours, for example, the difference in product yields would have been substantial.

EXAMPLE 7

Two reactions were performed using TMC hemithioketals of mercaptoethanol (TMCME) and 3-mercapto-1-propanol (TMCMP)[1]. A third reaction was performed using vinylic thioether of TMC and methyl 3-mercaptopropionate (TMCMMP)[2]. The reactions were examined in terms of reaction efficiency and yield.

Into a three-neck 500 ml round bottom flask equipped with an overhead stirrer, an HCl delivery tube, and an internal thermocouple, ketal (106.3 mmol) and molten phenol (45° C.; 637.6 mmol) were added with moderate stirring. HCl was bubbled directly into the reaction mixture at a rate of 0.6 mmol/min. The reaction temperatures, initially about 40° C., were allowed to gradually cool to room temperature. Each reaction was monitored as a function of time by gas chromatographic analyses. After 6 hours, the reaction mixtures were diluted with deionized water and suction filtered using a sintered glass Buchner funnel (4–5.5 μm pore diameter). The resulting filter cakes were triturated two times for one hour each using water at 80° C. The resulting products were dried for 16 hours in vacuo. The results are displayed in Table VII.

TABLE VII

| Run | Ratio[3] | | | Yield |
|---|---|---|---|---|
| | 2 hr | 4 hr | 6 hr | |
| TMCME | 16.78 | 6.41 | 2.91 | 62% |
| TMCMP | 14.21 | 8.96 | 2.96 | 48% |
| TMCMMP | 6.92 | 3.45 | 2.97 | 55% |

[1]TMC ketal of 3-mercapto-1-propanol:

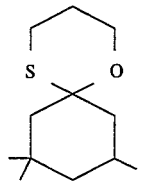

[2]Vinylic thioether of TMC and methyl-3-mercaptopropionate:

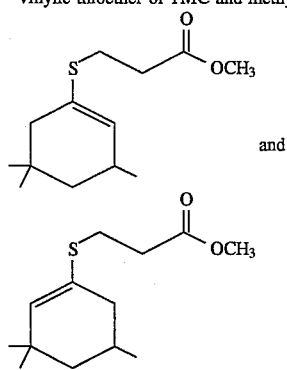

and

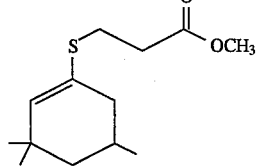

[3] Reaction aliquots were first silylated using N,O-bis(trimethylsilyl)acetamide in order to assay by gas chromatography. The "Ratio" heading represents the area % sum of starting materials (TMC/hemithioketal/vinylic thioether and silylated phenol) divided by the area % of product (silylated BPTMC).

EXAMPLE 8

Three reactions were performed using TMCME, TMCMP, and TMCMMP as co-catalysts. Three additional reactions were performed as controls using 1-decanethiol, mercaptoethanol, and 3-mercapto-1-propanol co-catalysts, respectively. The reactions were examined in terms of reaction efficiency and yield.

Into a three-neck 500 ml round bottom flask equipped with an overhead stirrer, an HCl delivery tube, and an internal thermocouple, TMC (106.3 mmol), molten phenol (45° C.; 637.6 mmol), and hemithioketal/1-decanethiol/mercaptoalkanol (10.6 mmol) were added with moderate stirring. HCl was bubbled directly into the reaction mixture at a rate of 0.6 mmol/min. The reaction temperatures, initially about 40° C., were allowed to gradually cool to room temperature. Each reaction was monitored as a function of time by gas chromatographic analyses. After 6 hours, the reaction mixtures were diluted with deionized water and suction filtered using a sintered glass Buchner funnel (4–5.5 μm pore diameter). The resulting filter cakes were triturated two times for one hour each using water at 80° C. The resulting products were dried for 16 hours in vacuo. The results are displayed in Table VIII.

TABLE VIII

| Run | Ratio* 2 hr | 4 hr | 6 hr | Yield |
|---|---|---|---|---|
| TMCME | 18.58 | 4.70 | 1.49 | 79% |
| TMCMP | 12.65 | 2.74 | 1.92 | 73% |
| TMCMMP | 11.87 | 1.62 | 1.50 | 83% |
| 1-decanethiol | 6.64 | 2.56 | 1.68 | 79% |
| mercaptoethanol | 8.76 | 2.03 | 1.54 | 84% |
| 3-mercapto-1-propanol | 5.85 | 2.37 | 1.42 | 80% |

*Reaction aliquots were first silylated using N,O-bis(trimethylsilyl)acetamide in order to assay by gas chromatography. The "Ratio" heading represents the area % sum of starting materials (TMC/hemithioketal and silylated phenol) divided by the area % of product (silylated BPTMC).

We claim:

1. A method of making 1,1-bis-(4-hydroxyphenyl)-3,3,5-trimethylcyclohexane ("BPTMC") which comprises contacting phenol with at least one starting material in the presence of an acid catalyst, said starting material having the formula:

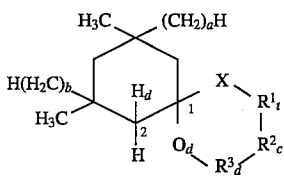

wherein,

X=oxygen or sulfur;

a=0,1; b=0,1; a+b=1;

c=0,1;

d=0,1; d≧c;

wherein, when d=0, there is a double bond between the number 1 and number 2 carbon of the ring;

t=0,1;

$R^1, R^2, R^3$ are independent of one another and are each an alkyl, —OH substituted alkyl, or —SH substituted alkyl group; and when c=0, $R^1$ and $R^3$ cannot be connected.

2. A method of making 1,1-bis-(4-hydroxyphenyl)-3,3,5-trimethylcyclohexane ("BPTMC") which comprises:

a) reacting 3,3,5-trimethylcyclohexanone with at least one alcohol having the formula:

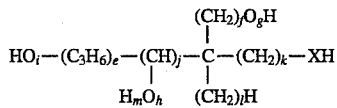

wherein:

e,g,h,j,k,l,m, and i=0,1 and are independent of one another except that: h≦j;

when k+f=0, g=0;

when e=0, i+h<2; m≧h; m≦j;

f=0,1,2; and

X is oxygen or sulfur, to produce at least one starting material having a formula selected from the group consisting of:

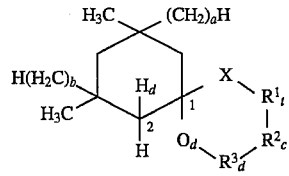

wherein, x=oxygen or sulfur;

a=0,1; b=0,1; a+b=1;

c=0,1;

d=0,1; d≧c;

wherein, when d=0, there is a double bond between the number 1 and number 2 carbon of the ring;

t=0,1;

$R^1, R^2, R^3$ are independent of one another and are each an alkyl, —OH substituted alkyl, or —SH substituted alkyl group;

and when c=0, $R^1$ and $R^3$ cannot be connected to each other; and b) contacting said starting material with phenol in the presence of an acid catalyst to obtain BPTMC and said alcohol.

3. The process of claim 2 wherein g+h+i=1 and X=oxygen.

4. The process of claim 2 wherein g+h+i=2 and X=sulfur.

5. The process of claim 2 wherein g+h+i≧1.

6. The process of claim 2 wherein g+h+i=0 and X=oxygen.

7. The process of claim 2 wherein X=sulfur.

8. The process of claim 2 wherein said alcohol used is selected from the group consisting of: ethylene glycol, propylene glycol, 1,3-propanediol, 2-methyl-1,3-propanediol, neopentyl glycol, 2,2,4-trimethyl-1,3-pentanediol, 2-ethyl-1,3-hexanediol, mercaptoethanol, 3-mercapto-1-propanol, 3-mercapto-1,2-propanediol, glycerol, and 2-ethylhexanol.

9. The process of claim 1 wherein said starting material is TMC ketal of ethylene glycol.

10. The process of claim 1 wherein said acid catalyst is HCl.

11. The process of claim 1 wherein an organosulfur co-catalyst is used.

12. The process of claim 1 wherein said phenol is present in a ratio of about 1:1 to 10:1 to the starting material.

13. The process of claim 1 wherein said acid catalyst is added to the reaction mixture at a rate of about 0.01 to 15 mol acid catalyst per mol starting material.

14. The method of claim 2 wherein said alcohol is recycled to step a.

* * * * *